United States Patent
Covey

(10) Patent No.: US 10,053,487 B2
(45) Date of Patent: *Aug. 21, 2018

(54) NEUROACTIVE 19-ALKOXY-17(20)-Z-VINYLCYANO-SUBSTITUTED STEROIDS, PRODRUGS THEREOF, AND METHODS OF TREATMENT USING SAME

(71) Applicant: Washington University, St. Louis, MO (US)

(72) Inventor: Douglas F. Covey, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,574

(22) Filed: Aug. 8, 2017

(65) Prior Publication Data

US 2017/0334944 A1 Nov. 23, 2017

Related U.S. Application Data

(63) Continuation of application No. 14/434,057, filed as application No. PCT/US2013/063473 on Oct. 4, 2013, now Pat. No. 9,765,110.

(60) Provisional application No. 61/710,844, filed on Oct. 8, 2012.

(51) Int. Cl.
C07J 41/00 (2006.01)
C07J 1/00 (2006.01)
C07J 21/00 (2006.01)

(52) U.S. Cl.
CPC .......... *C07J 41/0094* (2013.01); *C07J 1/0011* (2013.01); *C07J 21/008* (2013.01)

(58) Field of Classification Search
CPC ..... C07J 41/0094; C07J 1/0011; C07J 21/008
See application file for complete search history.

(56) References Cited

U.S. PATENT DOCUMENTS 9,765,110 B2 * 9/2017 Covey .................. C07J 41/0094
2015/0175651 A1 * 6/2015 Salituro ................ C07J 1/0029
552/531

FOREIGN PATENT DOCUMENTS

WO 2012116290 A2 8/2012

OTHER PUBLICATIONS

Shu, Hong-Jin et al., Characteristics of concatemeric GABAA receptors containing α4/δ subunits expressed in Xenopus oocytes, British Journal of Pharmacology, 2012, 165, pp. 2228-2243.
International Search Report and Written Opinion for PCT/US2013/063473, dated Feb. 20, 2014, 11 pgs.

* cited by examiner

*Primary Examiner* — Joseph R Kosack
(74) *Attorney, Agent, or Firm* — Armstrong Teasdale LLP

(57) ABSTRACT

The present disclosure is generally directed to neuroactive 19-alkoxy-17(20)-Z-vinylcyano-substituted steroids as referenced herein, and pharmaceutically acceptable salts thereof, for use as, for example, an anesthetic, and/or in the treatment of disorders relating to GABA function and activity. The present disclosure is further directed to pharmaceutical compositions comprising such compounds.

25 Claims, 3 Drawing Sheets

Displacement of Bound [$^{35}$S]-TBPS from GABA$_A$ Receptors by Compound 1

Potentiation of 2 mM GABA- Mediated Chloride Currents at Rat a1b2g2 type $GABA_A$ Receptors Expressed in Frog Oocytes by Different Concentrations of Compound 1

NEUROACTIVE 19-ALKOXY-17(20)-Z-VINYLCYANO-SUBSTITUTED STEROIDS, PRODRUGS THEREOF, AND METHODS OF TREATMENT USING SAME

CROSS-REFERENCE TO RELATED APPLICATION

This application is a continuation application of U.S. application Ser. No. 14/434,057, filed Apr. 7, 2015, which claims the benefit of U.S. National Phase Patent Application of International Application Serial Number PCT/US13/63473, filed Oct. 4, 2013, which claims the benefit of U.S. Provisional Patent Application Ser. No. 61/710,844, filed Oct. 8, 2012, the entire contents of which are incorporated herein by reference.

GOVERNMENT SUPPORT

This invention was made with government support under NIH Grant #GM047969, awarded by the National Institute of Health. The Government has certain rights in the invention.

BACKGROUND OF THE DISCLOSURE

The present disclosure is generally directed to novel compounds having utility as an anesthetic and/or in the treatment of disorders relating to GABA function and activity. More specifically, the present disclosure is directed to steroids having a 19-alkoxy-17(20)-Z-vinylcyano-substituted tetracyclic structure that are neuroactive and suitable for use as an anesthetic, as well as pharmaceutically acceptable salts and prodrugs thereof, and pharmaceutical compositions containing them.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. For example, it is now widely accepted that the intravenous anesthetic alphaxalone (Compound A, below) causes general anesthesia in humans because it allosterically increases chloride currents mediated by GABA acting at $GABA_A$ receptors in the brain. However, the various structural features that enable this compound to function in the way it does have, to-date, not been fully understood. For example, in contrast to alphaxalone, $\Delta^{16}$-alphaxalone (Compound B, below), has been observed to have greatly diminished allosteric activity at $GABA_A$ receptors and is not used as an intravenous general anesthetic in humans.

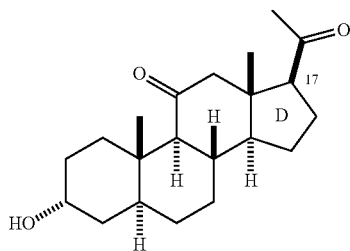

Compound A

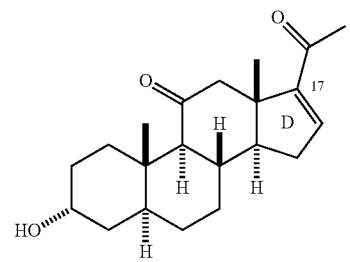

Compound B

The difference in performance of these two compounds, which some have attributed to the presence of the carbon-carbon double bond in the D-ring, has attracted the attention of many researchers. In fact, recently, it was determined that the effect this double bond has on anesthetic activity may depend on the group attached at C-17 on the D-ring. (See Bandyopadhyaya, A. K., et al., "Neurosteroid analogues. 15. A comparative study of the anesthetic and GABAergic actions of alphaxalone, $\Delta^{16}$-alphaxalone and their corresponding 17-carbonitrile analogues. Bioorg. Med. Chem. Lett., 20: 6680-4 (2010).)

In addition to anesthetic properties, neuroactive steroids may be used to treat disorders related to GABA function. For example, neuroactive steroids, such as progesterone, may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating steroids would exhibit anxiolytic effects. Neuroactive steroids may also be used to treat depression, given that accumulating evidence suggests that patients with major depression have decreased levels of GABAergic neurosteroids and that certain treatments for depression alter levels of these steroids. Although GABA is not typically thought to play a critical role in the biology of depression, there is evidence that low GABAergic activity may predispose one to mood disorders. Finally, inhibition of NMDA receptors and enhancement of $GABA_A$ receptors appear to play important roles in mediating the acute effects of ethanol in the nervous system, while related studies suggest that GABAergic neurosteroids may be involved in some of the pharmacological effects of ethanol and that neuroactive steroids may be useful in treating ethanol withdrawal.

In view of the foregoing, it is clear that there are a number of potentially advantageous uses for neurosteroids. As a result, there is a continuing need for the further synthesis and understanding of new neuroactive steroids, particularly those having utility as an anesthetic and/or in the treatment of a disorder relating to GABA function and activity.

SUMMARY OF THE DISCLOSURE

In one aspect, the present disclosure is directed to a compound having a structure of Formula (I):

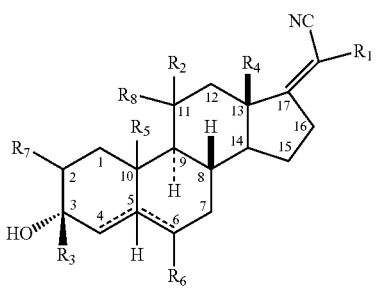

(I)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_3$ is H, optionally substituted $C_1$-$C_4$ alkyl, optionally substituted $C_2$-$C_4$ alkenyl, optionally substituted $C_2$-$C_4$ alkynyl, or optionally substituted aryl;
$R_4$ is independently selected from H and unsubstituted $C_1$-$C_4$ alkyl;
$R_5$ is substituted $C_1$-$C_4$ alkyl, optionally substituted $C_2$-$C_4$ alkenyl, or optionally substituted $C_2$-$C_4$ alkynyl (and in particular is alkoxy-substituted methyl, or even more particular is —$CH_2$—$OR_b$, where $R_b$ is $C_1$-$C_4$ alkyl, or even still more particularly is —$CH_2$—$OCH_3$);
$R_6$ is H, optionally substituted $C_1$-$C_4$ alkyl, or optionally substituted $C_1$-$C_4$ alkoxy;
$R_7$ is H, optionally substituted $C_1$-$C_4$ alkoxy, or an optionally substituted morpholinyl ring;
$R_8$, when present, is H or optionally substituted $C_1$-$C_4$ alkyl; and,
- - - denotes an optional, additional C—C bond, resulting in either a C=C bond between $C_4$-$C_5$ or $C_5$-$C_6$, with the proviso that when present, the $C_5$—H substituent is not present.

The present disclosure is further directed to a pharmaceutically acceptable salt of the noted compounds, or alternatively to prodrugs thereof. In one particular embodiment, the present disclosure is directed to a compound having a structure of Formula (II):

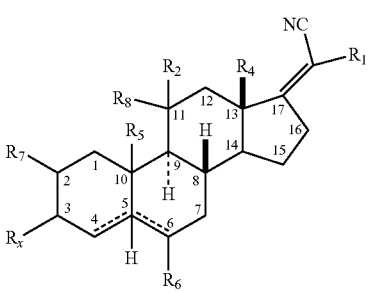

(II)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_x$ is =O or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration;
$R_4$ is independently selected from H and unsubstituted $C_1$-$C_4$ alkyl;
$R_5$ is substituted $C_1$-$C_4$ alkyl, optionally substituted $C_2$-$C_4$ alkenyl, or optionally substituted $C_2$-$C_4$ alkynyl (and in particular is alkoxy-substituted methyl, or even more particular is —$CH_2$—$OR_b$, where $R_b$ is $C_1$-$C_4$ alkyl, or even still more particularly is —$CH_2$—$OCH_3$);
$R_6$ is H, optionally substituted $C_1$-$C_4$ alkyl, or optionally substituted $C_1$-$C_4$ alkoxy;
$R_7$ is H, optionally substituted $C_1$-$C_4$ alkoxy, or an optionally substituted morpholinyl ring;
$R_8$, when present, is H or optionally substituted $C_1$-$C_4$ alkyl; and,
- - - denotes an optional, additional C—C bond, resulting in either a C=C bond between $C_4$-$C_5$ or $C_5$-$C_6$, with the proviso that when present, the $C_5$—H substituent is not present.

The present disclosure is still further directed to a pharmaceutical composition comprising a therapeutically effective amount of one or more of the above-noted steroids, or prodrugs, or pharmaceutically acceptable salts thereof, and optionally a pharmaceutically acceptable carrier. The present disclosure also provides kits comprising steroids, salts thereof, pro-drugs thereof, and/or pharmaceutical compositions thereof.

The present disclosure further provides methods of inducing anesthesia in a subject in need thereof, the method comprising administering to the subject a therapeutically effective amount of one or more of the above-noted steroids, or prodrugs, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

DETAILED DESCRIPTION OF CERTAIN EMBODIMENTS

Figure 1:
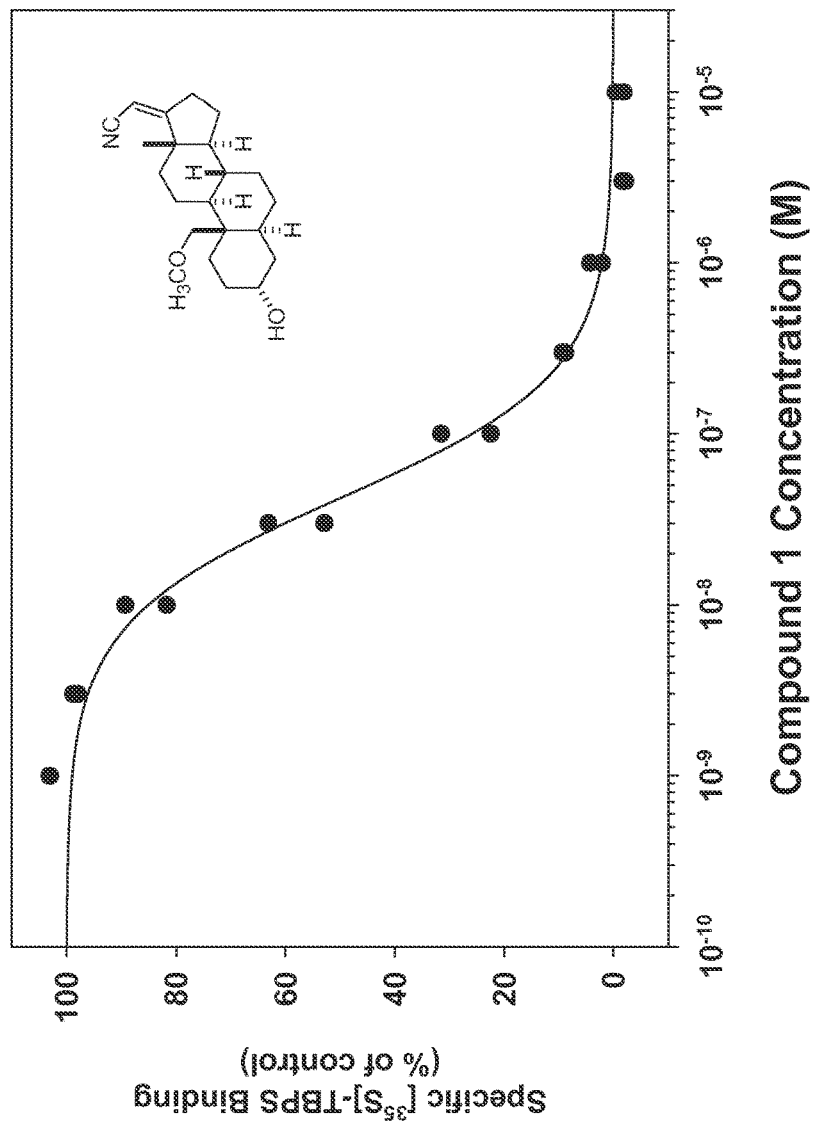
FIG. 1 is a graph illustrating the displacement of bound [$^{35}$S]-TBPS from $GABA_A$ receptors by Compound 1.

In accordance with the present disclosure, it has been discovered that compounds having a 17(20)-Z-vinylcyanosubstituted steroid structure, more specifically a 19-alkoxy-17(20)-Z-vinylcyano-substituted steroid structure, and even more specifically a 19-methoxy-17(20)-Z-vinylcyano-substituted steroid structure, are neuroactive and are also suitable for use as anesthetics and in the treatment of disorders associated with GABA function, as well as pharmaceutically acceptable salts and prodrugs thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1. Steroid Structure

Generally speaking, the steroid of the present disclosure has a tetracyclic, fused ring structure, such as a cyclopenta[a]phenanthrene ring system (an embodiment of which is illustrated and discussed in greater detail below), wherein the $C_3$-position of the A ring has a hydroxyl substituent in the α-position, and the $C_{17}$-position of the D ring has a vinyl-cyano (e.g., =CH(CN)) group, preferably in the Z-configuration, attached thereto. Notably, and as further detailed herein below, it has surprisingly been discovered that the activity of the steroids of the present disclosure are at least in part a function of the orientation or configuration of the carbon-carbon double bond of which $C_{17}$ is a part. More specifically, and as further illustrated below, it has been discovered that when this carbon-carbon double bond is in the Z-configuration (or cis-configuration), and further when the CN group is on the $C_{13}$ side of the molecule, the activity of the compound is notably higher, as compared to the alternative configuration (i.e., when the CN group is on the $C_{16}$ side of the molecule).

For example, comparison of the $IC_{50}$ values of the Compound 6a (the Z isomer) with Compound 6b (the E isomer) indicates that interchanging the relative positions of the C-20 substituents (H, CN) has a large effect on [$^{35}$S]-TBPS displacement potency. Compound 6a was about 17-fold more potent at displacing [$^{35}$S]-TBPS than Compound 6b. A comparison of the $IC_{50}$ values for Compounds 6a, 6b and 5c shows the effect that hydrogenation of the $\Delta^{17(20)}$ double bond present in Compound 6a and 6b has on binding potency. The change in conformation of the D-ring and the loss of the steric restraint imposed by the $\Delta^{17(20)}$ double bond increased the $IC_{50}$ value of Compound 5c about eight-fold relative to Compound 6a, and decreased the $IC_{50}$ value about twofold relative to Compound 6b. This disparity in displacement potency between Z and E isomers has also been observed in other 17-vinylcyano compounds studied, the Z isomer being about 10- to 20-fold more potent than the E isomer.

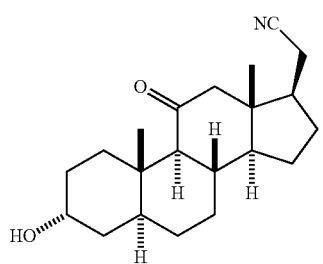

5c

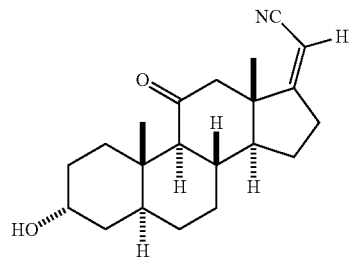

6a

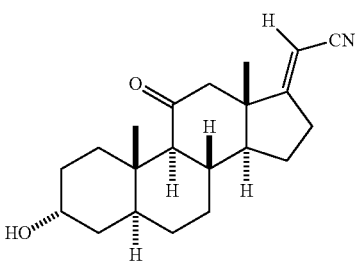

6b

More particularly, however, the present disclosure is directed, in certain embodiments, to a steroid having the structure of Formula (I):

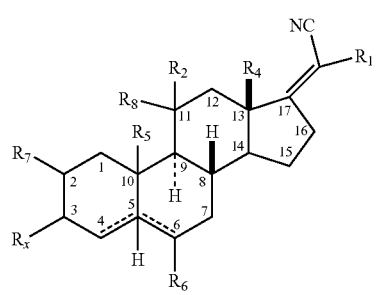

(I)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_3$ is H, optionally substituted $C_1$-$C_4$ alkyl, optionally substituted $C_2$-$C_4$ alkenyl, optionally substituted $C_2$-$C_4$ alkynyl, or optionally substituted aryl;
$R_4$ is independently selected from H and unsubstituted $C_1$-$C_4$ alkyl;
$R_5$ is substituted $C_1$-$C_4$ alkyl, optionally substituted $C_2$-$C_4$ alkenyl, or optionally substituted $C_2$-$C_4$ alkynyl (and in particular is alkoxy-substituted methyl, or even more particular is —$CH_2$—$OR_b$, where $R_b$ is $C_1$-$C_4$ alkyl, or even still more particularly is —$CH_2$—$OCH_3$);
$R_6$ is H, optionally substituted $C_1$-$C_4$ alkyl, or optionally substituted $C_1$-$C_4$ alkoxy;
$R_7$ is H, optionally substituted $C_1$-$C_4$ alkoxy, or an optionally substituted morpholinyl ring;
$R_8$, when present, is H or optionally substituted $C_1$-$C_4$ alkyl; and,
- - - denotes an optional, additional C—C bond, resulting in either a C=C bond between $C_4$-$C_5$ or $C_5$-$C_6$, with the proviso that when present, the $C_5$—H substituent is not present.

As generally defined above, $R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present. In certain embodiments, $R_2$ is =O and $R_8$ is not present. In certain embodiments, $R_2$ is H. In certain embodiments, $R_2$ is $OR_a$. In certain embodiments, $R_2$ is $OR_a$ and $R_a$ is optionally substituted $C_1$, $C_2$, $C_3$, or $C_4$ alkyl (e.g., methyl, ethyl), optionally substituted benzyl, or $C_1$, $C_2$, $C_3$, or $C_4$ alkyl substituted with O-aryl, such as O-benzyl. In certain embodiments, $R_2$ is $OR_a$ and $R_a$ is optionally substituted aryl. In certain embodiments, $R_2$ is $OR_a$ and $R_a$ is H.

As generally defined above, $R_3$ is H, optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, $R_3$ is H. In certain embodiments, $R_3$ is optionally substituted $C_1$, $C_2$, $C_3$ or $C_4$ alkyl (e.g., methyl, ethyl, trifluoromethyl, difluoromethyl). In certain embodiments, $R_3$ is methyl. In certain embodiments, $R_3$ is trifluoromethyl. In certain embodiments, $R_3$ is optionally substituted $C_2$, $C_3$ or $C_4$ alkenyl (e.g., optionally substituted allyl). In certain embodiments, $R_3$ is optionally substituted $C_2$, $C_3$, or $C_4$ alkynyl (e.g., optionally substituted acetylene or optionally substituted propargyl). In certain embodiments, $R_3$ is optionally substituted aryl (e.g., optionally substituted phenyl, such as phenyl substituted with OH, methyl, or $COR_c$, where $R_c$ is optionally substituted $C_1$-$C_{22}$ alkyl or optionally substituted $C_2$-$C_{22}$ alkenyl, including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl).

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is substituted $C_1$-$C_4$ alkyl, optionally substituted $C_2$-$C_4$ alkenyl, or optionally substituted $C_2$-$C_4$ alkynyl. In certain embodiments, $R_5$ is substituted $C_1$-$C_4$ alkyl, and in particular is alkoxy-substituted $C_1$-$C_4$ alkyl. In other particular embodiments, $R_5$ is substituted methyl, and more particularly is alkoxy-substituted methyl (or even more particularly is —$CH_2$—$OR_b$, where $R_b$ is $C_1$-$C_4$ alkyl, or even still more particularly is —$CH_2$—$OCH_3$). In other embodiments, $R_5$ is optionally substituted $C_2$-$C_4$ alkenyl. In other embodiments, $R_5$ is optionally substituted $C_2$-$C_4$ alkynyl. In certain embodiments, $R_5$ is in the beta (up) position.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl). In certain embodiments, $R_6$ is optionally substituted $C_1$, $C_2$, $C_3$ or $C_4$ alkoxy (e.g., methoxy, ethoxy, n-propyloxy, isopropyloxy, or n-butoxy). In certain embodiments, when $R_6$ is a non-hydrogen group, $R_6$ is in the alpha (down) position. In certain preferred embodiments, however, when $R_6$ is a non-hydrogen group, $R_6$ is in the beta (up) position.

As generally defined above, $R_7$ is H, optionally substituted $C_1$-$C_4$ alkoxy, or an optionally substituted morpholinyl ring. In certain embodiments, $R_7$ is H. In certain embodiments, $R_7$ is optionally substituted $C_1$, $C_2$, $C_3$ or $C_4$ alkoxy (e.g., methoxy, ethoxy, n-propyloxy, isopropyloxy, or n-butoxy). In certain embodiments, $R_7$ is an optionally substituted morpholinyl ring. In certain embodiments, when $R_7$ is a non-hydrogen group, $R_7$ is in the alpha (down) position. In certain preferred embodiments, however, when $R_7$ is a non-hydrogen group, $R_7$ is in the beta (up) position.

As generally defined above, $R_8$, when present, is H or optionally substituted $C_1$-$C_4$ alkyl. In certain embodiments, $R_8$ is H. In certain embodiments, $R_8$ is $C_1$, $C_2$, $C_3$ or $C_4$ optionally substituted alkyl (e.g., methyl). In certain embodiments, when $R_8$ is optionally substituted $C_1$-$C_4$ alkyl, $R_8$ is in the alpha (down) position. In certain embodiments, when $R_8$ is optionally substituted $C_1$-$C_4$ alkyl, $R_8$ is in the beta (up) position.

In certain embodiments, $R_2$ and $R_8$ are both H. In certain embodiments, $R_2$ is $OR_a$ and $R_8$ is H.

As generally defined above, - - - denotes an optional, additional C—C bond, resulting in either a C=C bond between $C_4$-$C_5$ or $C_5$-$C_6$, with the proviso that when present, the $C_5$—H substituent is not present. In certain embodiments, the additional C—C bond is absent, and the hydrogen at $C_5$ is in the alpha or beta position. In certain embodiments, the additional C—C bond is absent, and the hydrogen at $C_5$ is in the alpha (down) position. In certain embodiments, the additional C—C bond is absent, and the hydrogen at $C_5$ is in the beta (up) position. In certain embodiments, - - - denotes an additional C—C bond, resulting in a C=C bond between $C_4$-$C_5$. In certain embodiments, - - - denotes an additional C—C bond, resulting in a C=C bond between $C_5$-$C_6$.

It is to be noted that the present disclosure contemplates and is intended to encompass all of the various combinations and permutations (i.e., combinations of substituent options, locations and stereochemical configurations) possible here.

For example, in various embodiments, compounds of the present disclosure may be selected from among those encompassed by the structure of Formula (I), wherein $R_2$ is =O; alternatively, $R_2$ may be H and $R_8$ is H (e.g., $C_{11}$ thus having two hydrogen atoms bound thereto as substituents). In certain embodiments, $R_2$ may be $OR_a$, wherein $R_a$ is methyl, optionally substituted benzyl, or $C_1$-$C_4$ alkyl substituted with O-aryl, such as O-benzyl. In certain embodiments, $R_3$ may be H, methyl, trifluoromethyl, or substituted aryl (e.g., substituted phenyl, which in turn may be optionally substituted such as, for example, with OH, methyl, or $COR_c$, where $R_c$=$C_1$-$C_4$ alkyl); further, when $R_3$ is something other than H, $R_3$ is preferably in the β-position. In certain embodiments, each of $R_4$ and $R_6$ are independently selected from H and methyl, $R_5$ being in the β-configuration and $R_6$ optionally being in the α-configuration or β-configuration (e.g., when $R_6$ is methyl), which the β-configuration being preferred. In certain embodiments, $R_7$ is selected from H, methoxy, ethoxy, and an optionally substituted morpholinyl ring; further, when $R_7$ is something other than H, $R_7$ is preferably in the β-position. In certain embodiments, $R_8$, when present, is selected from H or optionally substituted $C_1$-$C_4$ alkyl. In certain embodiments, $R_8$ is methyl (e.g., methyl in the alpha-configuration).

In certain embodiments, the $C_5$—H is in the alpha configuration and the $R_5$ is, for example, a substituted methyl group (e.g., alkoxy-substituted methyl, or in particular a methoxy-substituted methyl) in the beta configuration. In certain embodiments, the C5-H is in the beta configuration and $R_5$ is, for example, a substituted methyl (e.g., a methoxy-substituted methyl) group in the beta configuration. In certain embodiments, $R_6$ is H. In certain embodiments, $R_4$ is methyl. In certain embodiments, $R_2$ is =O or methoxy.

Accordingly, as noted, the steroid of Formula (I) may encompass a number of various structures in accordance with the present disclosure.

In certain embodiments, wherein $R_1$ is H, $R_3$ is in the beta position, $R_4$ is methyl, $R_5$ is substituted methyl in the beta position, and $R_6$ is H, provided is a compound of Formula (I-a):

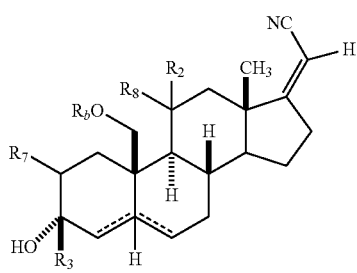

(I-a)

or a pharmaceutically acceptable salt thereof, wherein - - - , $R_2$, $R_3$, $R_7$ and $R_8$ are as defined herein, and further wherein $R_b$ is optionally substituted $C_1$-$C_4$ alkyl. In certain embodiments, each instance of - - - is absent and $C_5$—H is in the alpha position. In certain embodiments, each instance of - - - is absent and $C_5$—H is in the beta position.

In certain embodiments of Formula (I), wherein $R_2$ is =O and $R_8$ is absent, provided is a compound of Formula (I-b):

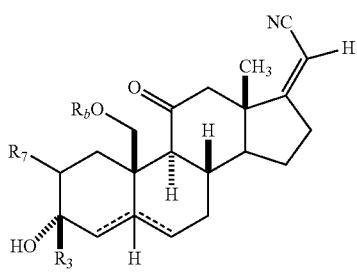

(I-b)

or a pharmaceutically acceptable salt thereof, wherein - - - , $R_3$ and $R_7$ are as defined herein, and further wherein $R_b$ is optionally substituted $C_1$-$C_4$ alkyl. In certain embodiments, each instance of - - - is absent and $C_5$—H is in the alpha position. In certain embodiments, each instance of - - - is absent and $C_5$—H is in the beta position.

In certain embodiments of Formula (I), wherein $R_2$ and $R_8$ are H, provided is a compound of Formula (I-c):

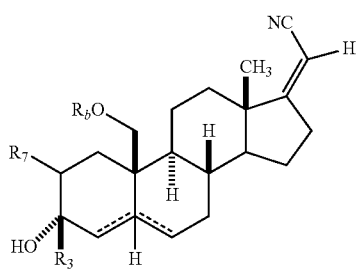

(I-c)

or a pharmaceutically acceptable salt thereof, wherein - - - , $R_2$, $R_3$, and $R_7$ are as defined herein, and further wherein $R_b$ is optionally substituted $C_1$-$C_4$ alkyl. In certain embodiments, each instance of - - - is absent and $C_5$—H is in the alpha position. In certain embodiments, each instance of - - - is absent and $C_5$—H is in the beta position.

In certain embodiments of Formula (I), wherein $R_2$ is $OR_a$ and $R_8$ is H, provided is a compound of Formula (I-d):

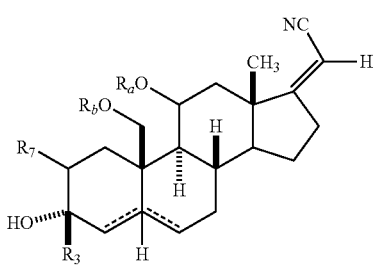

(I-d)

or a pharmaceutically acceptable salt thereof, wherein - - - , $R_3$, $R_7$, and $R_a$ are as defined herein, and further wherein $R_b$ is optionally substituted $C_1$-$C_4$ alkyl. In certain embodiments, each instance of - - - is absent and $C_5$—H is in the alpha position. In certain embodiments, each instance of - - - is absent and $C_5$—H is in the beta position.

In certain embodiments of Formula (I), wherein $R_7$ is H, provided is a compound of Formula (I-e):

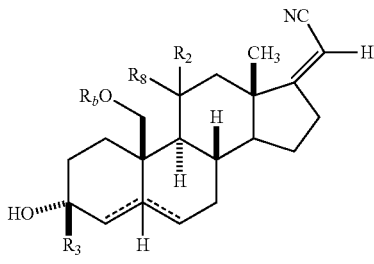

(I-e)

or a pharmaceutically acceptable salt thereof, wherein - - - , $R_2$, $R_3$, and $R_8$ are as defined herein, and further wherein $R_b$ is optionally substituted $C_1$-$C_4$ alkyl. In certain embodiments, each instance of - - - is absent and $C_5$—H is in the alpha position. In certain embodiments, each instance of - - - is absent and $C_5$—H is in the beta position.

In certain embodiments of Formula (I), wherein each instance of - - - is absent and $C_5$—H is in the alpha position, provided is a compound of Formula (I-f):

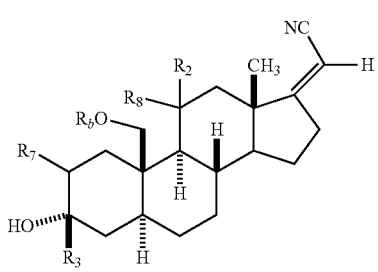

(I-f)

or a pharmaceutically acceptable salt thereof, wherein $R_2$, $R_3$, $R_7$ and $R_8$ are as defined herein, and further wherein $R_b$ is optionally substituted $C_1$-$C_4$ alkyl.

In certain embodiments of Formula (I), wherein $R_7$ is H, provided is a compound of Formula (I-g):

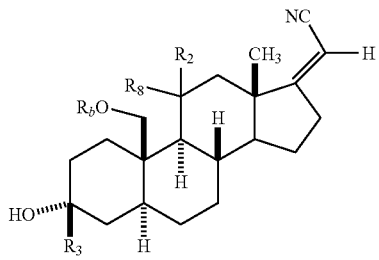

or a pharmaceutically acceptable salt thereof, wherein $R_2$, $R_3$, and $R_8$ are as defined herein, and further wherein $R_b$ is optionally substituted $C_1$-$C_4$ alkyl.

In certain embodiments of Formula (I), wherein $R_2$ is =O, provided is a compound of Formula (I-h):

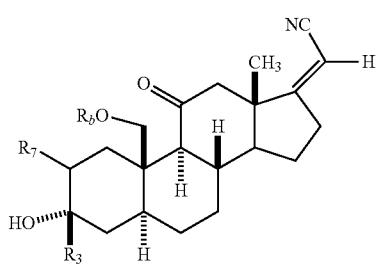

or a pharmaceutically acceptable salt thereof, wherein $R_3$ and $R_7$ are as defined herein, and further wherein $R_b$ is optionally substituted $C_1$-$C_4$ alkyl.

In certain embodiments of Formula (I), wherein $R_2$ is $OR_a$, provided is a compound of Formula (I-i):

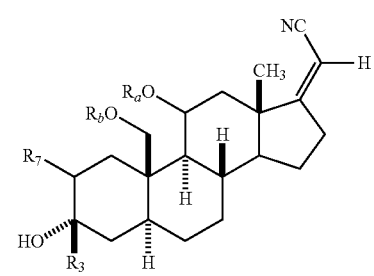

or a pharmaceutically acceptable salt thereof, wherein $R_a$, $R_3$, and $R_7$ are as defined herein, and further wherein $R_b$ is optionally substituted $C_1$-$C_4$ alkyl.

In certain embodiments of Formula (I), wherein - - - represents an additional C—C bond, resulting in a C=C bond between $C_4$-$C_5$ provided is a compound of Formula (I-j):

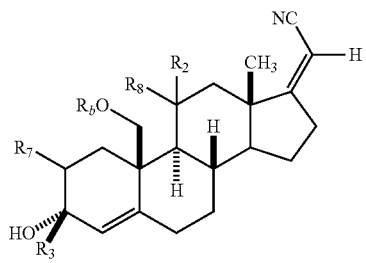

or a pharmaceutically acceptable salt thereof, wherein $R_3$, $R_2$, $R_7$ and $R_8$ are as defined herein, and further wherein $R_b$ is optionally substituted $C_1$-$C_4$ alkyl.

In certain embodiments of Formula (I), wherein - - - represents an additional C—C bond, resulting in a C=C bond between $C_5$-$C_6$ provided is a compound of Formula (I-k):

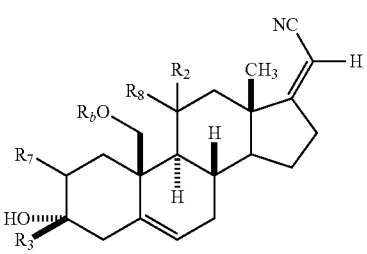

or a pharmaceutically acceptable salt thereof, wherein $R_3$, $R_2$, $R_7$ and $R_8$ are as defined herein, and further wherein $R_b$ is optionally substituted $C_1$-$C_4$ alkyl.

Exemplary compounds of Formula (I) include, but are not limited to, the following:

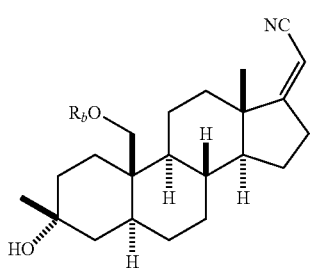

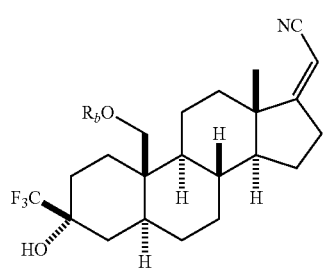

-continued
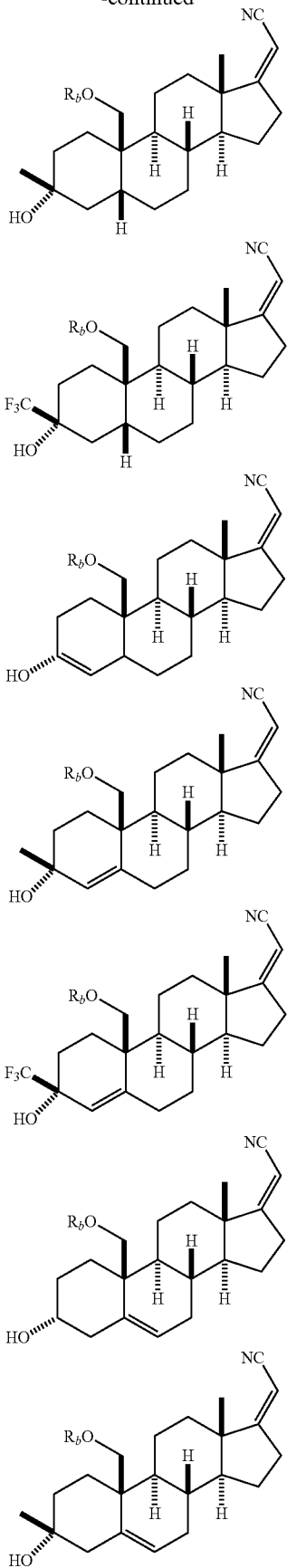
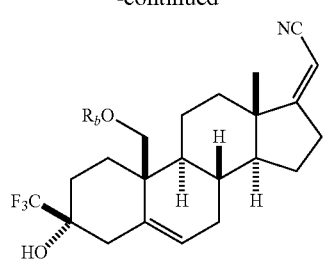
and pharmaceutically acceptable salts thereof.
In certain embodiments, the steroid of Formula (I) is selected from the group consisting of:
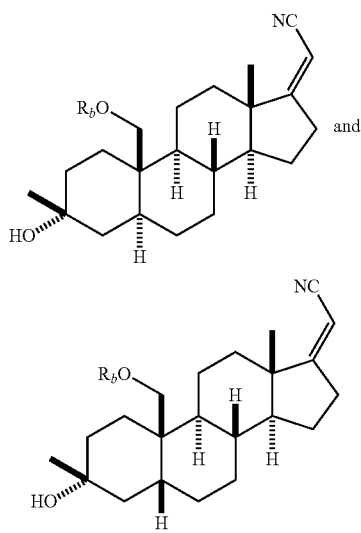
and pharmaceutically acceptable salts thereof.
In certain embodiments, the steroid of Formula (I) is selected from the group consisting of:
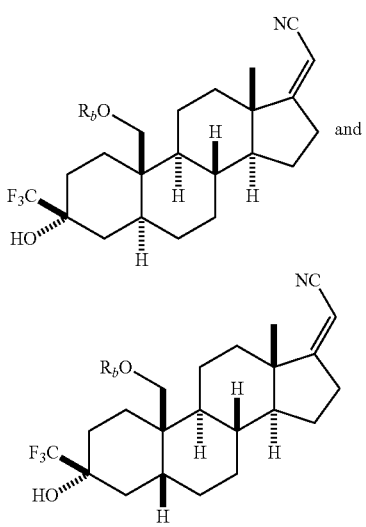
and pharmaceutically acceptable salts thereof.

In certain embodiments, the steroid of Formula (I) is selected from the group consisting of:

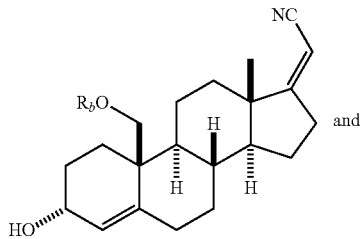

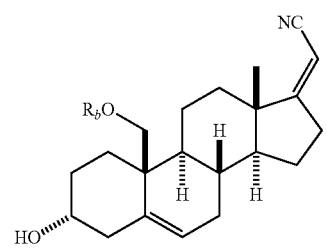

or a pharmaceutically acceptable salt thereof.

In certain embodiments, the steroid of Formula (I) is selected from the group consisting of:

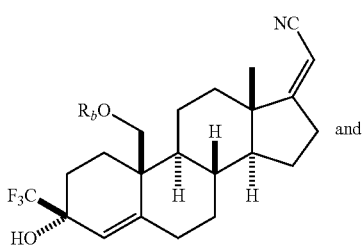

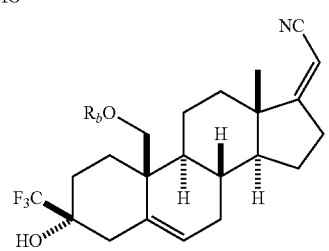

and pharmaceutically acceptable salts thereof.

In certain embodiments, the steroid of Formula (I) is selected from the group consisting of:

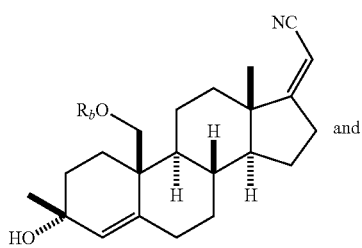

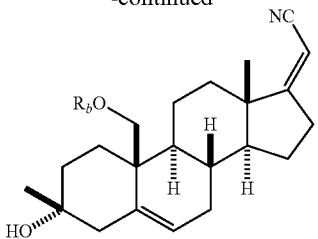

and pharmaceutically acceptable salts thereof, wherein $R_b$ is as defined herein.

In this regard it is to be noted that the structures provided above are of various exemplary embodiments. As such, they should not be viewed in a limiting sense.

2. Prodrug Structure

In another particular embodiment, the present disclosure is in general directed to prodrugs of the various steroids detailed above. Generally speaking, as used herein, a "prodrug" refers to an inactive, or significantly less active, form of the steroids detailed above (and in particular the steroids of Formula (I)), which after administration is metabolized in vivo into one or more active metabolites of the steroid of Formula (I). The prodrug may be formed using means generally known in the art, and therefore may take essentially any form that would be recognized to one of ordinary skill in the art. The prodrugs of the present disclosure may advantageously provide improved absorption, distribution, metabolism and/or excretion optimization, as well as improved oral bioavailability of the steroids detailed above (and in particular the steroids of Formula (I)).

In another particular embodiment of the present disclosure the prodrug of a steroid disclosed herein has a structure of Formula (II):

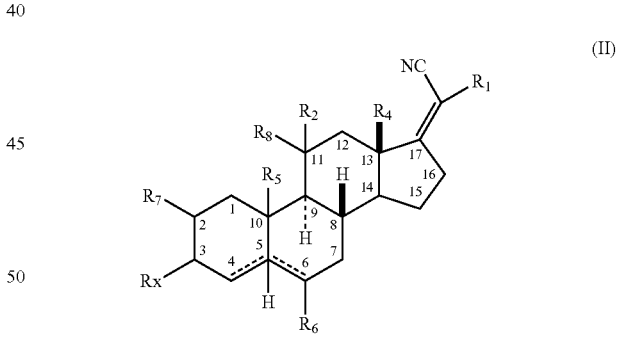

(II)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_x$ is =O or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration (and when $R_x$ is $R_d$, with $R_d$ being $C(O)R_e$, then it is preferably in the beta configuration);
$R_4$ is independently selected from H and unsubstituted $C_1$-$C_4$ alkyl;

$R_5$ is substituted $C_1$-$C_4$ alkyl, optionally substituted $C_2$-$C_4$ alkenyl, or optionally substituted $C_2$-$C_4$ alkynyl (and in particular is alkoxy-substituted methyl, or even more particular is —CH$_2$—OR$_b$, where R$_b$ is $C_1$-$C_4$ alkyl, or even still more particularly is —CH$_2$—OCH$_3$);

$R_6$ is H, optionally substituted $C_1$-$C_4$ alkyl, or optionally substituted $C_1$-$C_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl; and,

- - - denotes an optional, additional C—C bond, resulting in either a C═C bond between $C_4$-$C_5$ or $C_5$-$C_6$, with the proviso that when present, the $C_5$—H substituent is not present.

In this regard, it is to be noted that the present disclosure contemplates and is intended to encompass all of the various combinations and permutations (i.e., combinations of substituent options, locations and stereochemical configurations) possible here.

As generally defined above, $R_x$ is ═O or OR$_d$, where R$_d$ is H or C(O)R$_e$, where R$_e$ is optionally substituted $C_1$-$C_{22}$ alkyl or optionally substituted $C_2$-$C_{22}$ alkenyl (including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl), with the proviso that when R$_x$ is OH, it is in the beta (up) configuration. In certain embodiments, R$_x$ is ═O. In certain embodiments, R$_x$ is OH in the beta (up) configuration. In certain embodiments, R$_x$ is OR$_d$, R$_d$ is C(O)R$_e$, and R$_e$ is optionally substituted $C_1$-$C_{22}$ alkyl or optionally substituted $C_2$-$C_{22}$ alkenyl, e.g., C(O)CH$_3$, and in such instances, the group Rx is provided in either the alpha or beta configuration (with the beta configuration being preferred0. In certain embodiments, wherein R$_x$ is OR$_d$, and R$_d$ is H, then R$_x$ is OH in the beta (up) configuration.

As generally defined above, $R_2$ is ═O, H, or OR$_a$, where R$_a$ is selected from H, optionally substituted $C_1$-$C_4$ alkyl, or optionally substituted aryl, with the proviso that when $R_2$ is ═O, R$_8$ is not present. In certain embodiments, $R_2$ is ═O and R$_8$ is not present. In certain embodiments, $R_2$ is H. In certain embodiments, $R_2$ is OR$_a$. In certain embodiments, $R_2$ is OR$_a$ and R$_a$ is optionally substituted $C_1$, $C_2$, $C_3$ or $C_4$ alkyl (e.g., methyl, ethyl), optionally substituted benzyl, or $C_1$, $C_2$, $C_3$ or $C_4$ alkyl substituted with O-aryl, such as O-benzyl. In certain embodiments, $R_2$ is OR$_a$ and R$_a$ is optionally substituted aryl. In certain embodiments, $R_2$ is OR$_a$ and R$_a$ is H.

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is substituted $C_1$-$C_4$ alkyl, optionally substituted $C_2$-$C_4$ alkenyl, or optionally substituted $C_2$-$C_4$ alkynyl. In certain embodiments, $R_5$ is substituted $C_1$-$C_4$ alkyl, and in particular is alkoxy-substituted $C_1$-$C_4$ alkyl. In other particular embodiments, $R_5$ is substituted methyl, and more particularly is alkoxy-substituted methyl (or even more particularly is —CH$_2$—OR$_b$, where R$_b$ is $C_1$-$C_4$ alkyl, or even still more particularly is —CH$_2$—OCH$_3$). In other embodiments, $R_5$ is optionally substituted $C_2$-$C_4$ alkenyl. In other embodiments, $R_5$ is optionally substituted $C_2$-$C_4$ alkynyl. In certain embodiments, $R_5$ is in the beta (up) position.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl).

In certain embodiments, $R_6$ is optionally substituted $C_1$, $C_2$, $C_3$ or $C_4$ alkoxy (e.g., methoxy, ethoxy, n-propyloxy, isopropyloxy, or n-butoxy). In certain embodiments, when $R_6$ is a non-hydrogen group, $R_6$ is in the alpha (down) position. In certain preferred embodiments, however, when $R_6$ is a non-hydrogen group, $R_6$ is in the beta (up) position.

As generally defined above, $R_7$ is H, optionally substituted $C_1$-$C_4$ alkoxy, or an optionally substituted morpholinyl ring. In certain embodiments, $R_7$ is H. In certain embodiments, $R_7$ is optionally substituted $C_1$, $C_2$, $C_3$ or $C_4$ alkoxy (e.g., methoxy, ethoxy, n-propyloxy, isopropyloxy, or n-butoxy). In certain embodiments, $R_7$ is an optionally substituted morpholinyl ring. In certain embodiments, when $R_7$ is a non-hydrogen group, $R_7$ is in the alpha (down) position. In certain preferred embodiments, however, when $R_7$ is a non-hydrogen group, $R_7$ is in the beta (up) position.

As generally defined above, $R_8$, when present, is H or optionally substituted $C_1$-$C_4$ alkyl. In certain embodiments, $R_8$ is H. In certain embodiments, $R_8$ is $C_1$, $C_2$, $C_3$ or $C_4$ optionally substituted alkyl (e.g., methyl). In certain embodiments, when $R_8$ is optionally substituted $C_1$-$C_4$ alkyl, $R_8$ is in the alpha (down) position. In certain embodiments when $R_8$ is optionally substituted $C_1$-$C_4$ alkyl, $R_8$ is in the beta (up) position.

In certain embodiments, $R_2$ and $R_8$ are both H. In certain embodiments, $R_2$ is OR$_a$ and $R_8$ is H.

As generally defined above, - - - denotes an optional, additional C—C bond, resulting in either a C═C bond between $C_4$-$C_5$ or $C_5$-$C_6$, with the proviso that when present, the $C_5$—H substituent is not present. In certain embodiments, the additional C—C bond is absent, and the hydrogen at $C_5$ is in the alpha or beta position. In certain embodiments, the additional C—C bond is absent, and the hydrogen at $C_5$ is in the alpha (down) position. In certain embodiments, the additional C—C bond is absent, and the hydrogen at $C_5$ is in the beta (up) position. In certain embodiments, - - - denotes an additional C—C bond, resulting in a C═C bond between $C_4$-$C_5$. In certain embodiments, - - - denotes an additional C—C bond, resulting in a C═C bond between $C_5$-$C_6$.

In certain embodiments, prodrugs of the present disclosure may be selected from among those encompassed by the structure of Formula (II), wherein $R_2$ is ═O. In certain embodiments, $R_2$ is H and $R_8$ is H, e.g., $C_{11}$ thus having two hydrogen atoms bound thereto as substituents. In certain embodiments, $R_2$ may be OR$_a$, wherein R$_a$ is methyl, optionally substituted benzyl, or $C_1$-$C_4$ alkyl substituted with O-aryl, such as O-benzyl. In certain embodiments, $R_x$ is ═O. In certain embodiments, $R_x$ is β-hydroxy. In certain embodiments, $R_x$ is OR$_d$, where R$_d$ is H or C(O)R$_e$, where R$_e$ is optionally substituted $C_1$-$C_4$ alkyl (e.g., methyl). In certain embodiments, each of $R_4$ and $R_6$ are independently selected from H and methyl. In certain embodiments, $R_5$ is in the beta-configuration. In certain embodiments, $R_6$ is optionally substituted alkyl, e.g., methyl, optionally in the alpha-configuration when the carbon-carbon double bond between $C_5$-$C_6$ is absent. In certain embodiments, $R_6$ is optionally substituted alkyl, e.g., methyl, optionally in the beta-configuration when the carbon-carbon double bond between $C_5$-$C_6$ is absent. In certain embodiments, $R_7$ is selected from H, methoxy, ethoxy, and an optionally substituted morpholinyl ring. In certain embodiments, $R_7$ is a non-hydrogen group, $R_7$ is in the β-position. In certain embodiments, a carbon-carbon double bond (or unsaturated bond) may be present between the $C_4$-$C_5$, or $C_5$-$C_6$, carbon atoms. In certain embodiments, $R_8$, when present, is selected from H or optionally substituted $C_1$-$C_4$ alkyl, preferably methyl and more preferably alpha-methyl.

In certain embodiments, $R_x$ is OH and in the beta position. In certain embodiments, a carbon-carbon double bond is present between the $C_4$-$C_5$ carbon atoms. In certain embodiments, a carbon-carbon double bond is present between the $C_5$-$C_6$ carbon atoms. In certain embodiments, $R_2$ is =O. In certain embodiments, $R_2$ is methoxy. In certain embodiments, $R_7$ is H. In certain embodiments, $R_7$ is β-methoxy. In certain embodiments, $R_7$ is β-ethoxy.

In certain embodiments, wherein $R_4$ is methyl, $R_5$ is substituted methyl in the beta position, and $R_6$ is H, provided is a compound of Formula (II-a):

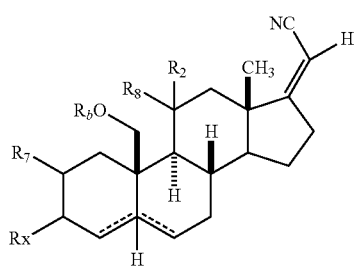

(II-a)

or a pharmaceutically acceptable salt thereof, wherein - - -, $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - is absent and $C_5$—H is in the alpha position. In certain embodiments, each instance of - - - is absent and $C_5$—H is in the beta position. In certain embodiments, - - - represents an additional C—C bond, resulting in either a C=C bond between $C_4$-$C_5$ or $C_5$-$C_6$.

In certain embodiments of Formula (II), wherein $R_2$ is =O and $R_8$ is absent, provided is a compound of Formula (II-b):

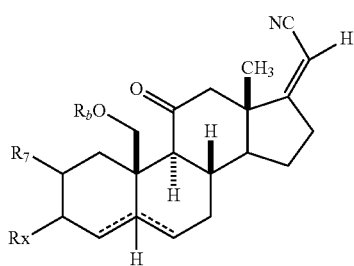

(II-b)

or a pharmaceutically acceptable salt thereof, wherein - - -, $R_x$, and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II), wherein $R_2$ is H and $R_8$ is H, provided is a compound of Formula (II-c):

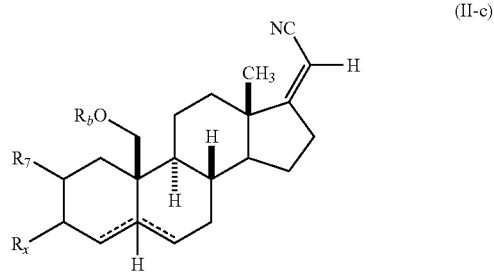

(II-c)

or a pharmaceutically acceptable salt thereof, wherein - - -, $R_x$, and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II), wherein $R_2$ is $OR_a$ and $R_8$ is H, provided is a compound of Formula (II-d):

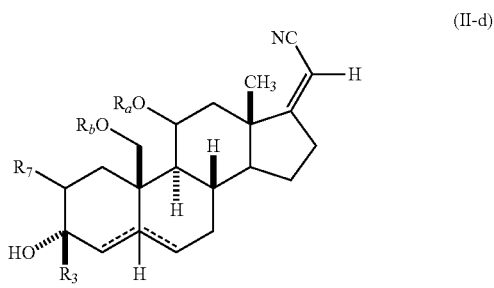

(II-d)

or a pharmaceutically acceptable salt thereof, wherein - - -, $R_3$, $R_7$ (preferably in the beta configuration), and $R_a$ are as defined herein, and further wherein $R_b$ is optionally substituted $C_1$-$C_4$ alkyl. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II), wherein $R_7$ is H, provided is a compound of Formula (II-e):

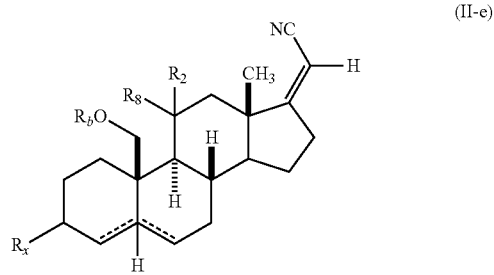

(II-e)

or a pharmaceutically acceptable salt thereof, wherein - - -, $R_x$, $R_2$ and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II), wherein each instance of - - - is absent $C_5$—H is in the alpha position, provided is a compound of Formula (II-f):

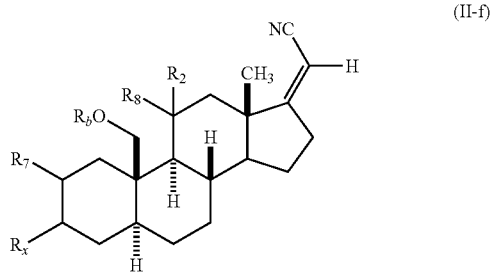

(II-f)

or a pharmaceutically acceptable salt thereof, wherein $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

In certain embodiments of Formula (II), wherein $R_7$ is H, provided is a compound of Formula (II-g):

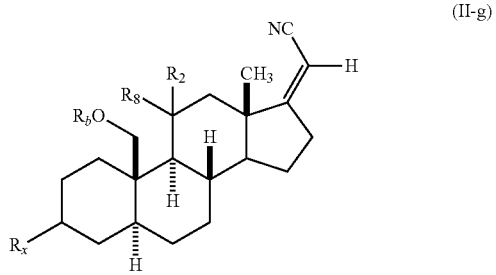

(II-g)

or a pharmaceutically acceptable salt thereof, wherein $R_x$, $R_2$ and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

In certain embodiments of Formula (II), wherein $R_2$ is =O, provided is a compound of Formula (II-h):

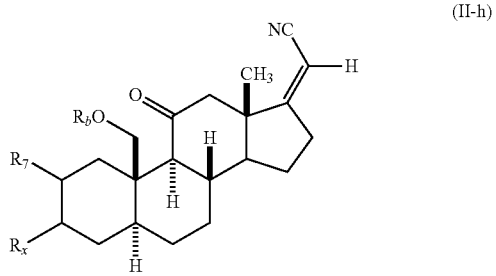

(II-h)

or a pharmaceutically acceptable salt thereof, wherein $R_x$ and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

In certain embodiments of Formula (II), wherein $R_2$ is $OR_a$, provided is a compound of Formula (II-i):

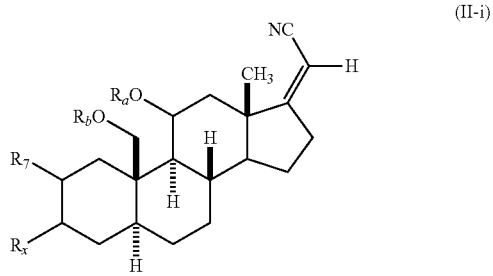

(II-i)

or a pharmaceutically acceptable salt thereof, wherein $R_x$, $R_a$, and $R_7$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

In certain embodiments of Formula (II), - - - represents an additional C—C bond, resulting in a C=C bond between $C_4$-$C_5$ provided is a compound of Formula (II-j):

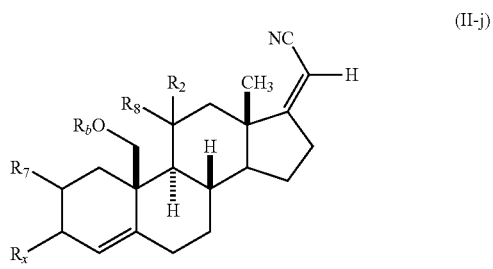

(II-j)

or a pharmaceutically acceptable salt thereof, wherein $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

In certain embodiments of Formula (II), wherein - - - represents an additional C—C bond, resulting in a C=C bond between $C_5$-$C_6$ provided is a compound of Formula (II-k):

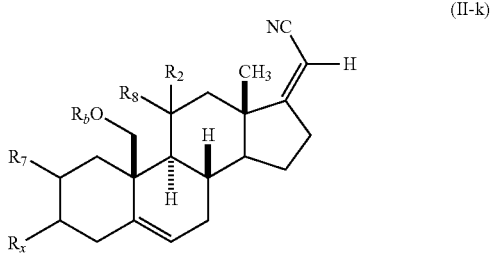

(II-k)

or a pharmaceutically acceptable salt thereof, wherein $R_x$, $R_2$, $R_7$ (preferably in the beta configuration) and $R_8$ (preferably in the beta configuration) are as defined herein, and further wherein $R_b$ is optionally substituted $C_1$-$C_4$ alkyl. In certain embodiments, $R_x$ is =O. In certain embodiments, $R_x$ is OH in the beta (up) configuration.

Exemplary compounds of Formula (II) include, but are not limited to:

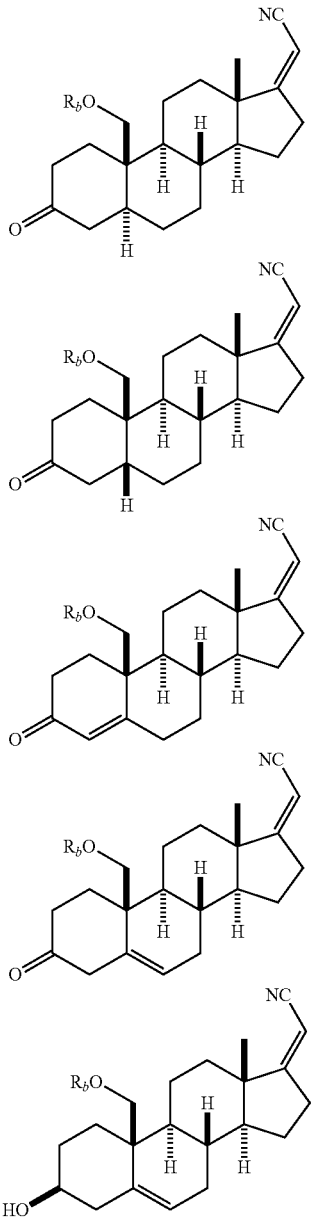

and pharmaceutically acceptable salts thereof.

In this regard it is to be noted that the structures provided above are of various exemplary embodiments. As such, they should not be viewed in a limiting sense.

3. Methods of Preparation and Pharmaceutical Compositions

It is to be noted that the compounds or steroids of the present disclosure, or the prodrugs thereof, may in various embodiments be prepared or used in accordance with means generally known in the art. For example, in certain embodiments, the steroids or prodrugs of the present disclosure may be prepared or used in a pharmaceutically acceptable salt form, for example, where $R_7$ is an optionally substituted morpholinyl ring. Suitable salt forms include, for example, citrate or chloride salt forms.

In various embodiments of the present disclosure, a pharmaceutical composition is disclosed that may comprise a steroid, a prodrug, or a combination of two or more thereof in accordance with the formulas of the present disclosure. The compounds or steroids of the present disclosure (or the prodrugs thereof), as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or steroids of the present disclosure are useful for potentiating GABA at $GABA_A$ receptors thereby inducing anesthesia or treating disorders related to GABA function (e.g., insomnia, mood disorders, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted steroids, or prodrugs, or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or steroids of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The compounds, steroids, and prodrugs of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.,) (Marcel Dekker, Inc., New York, N.Y., 1980), Remington's Pharmaceutical Sciences (A. Gennaro, ed., 19th ed.)(Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the invention are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

4. Definitions

The term "steroid" as used herein describes an organic compound containing in its chemical nucleus the cyclopenta[a]phenanthrene ring system.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "prodrug" as used herein describes a pharmacological substance that is administered in a less active or inactive form. After administration, a prodrug is metabolized in vivo e.g., via hydrolysis, oxidation, or reaction under biological conditions (in vitro or in vivo), to provide an active metabolite. See, e.g., Wu, *Pharmaceuticals* (2009) 2:77-81. In certain embodiments, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract or the skin, or it may enhance drug stability for long-term storage.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the subject is a human.

As used herein, a "therapeutically effective amount" "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "$C_{1-4}$ alkyl" is intended to encompass, $C_1$, $C_2$, $C_3$, $C_4$, $C_{1-3}$, $C_{1-2}$, $C_{2-4}$, $C_{2-3}$ and $C_{3-4}$ alkyl, while "$C_{1-22}$ alkyl" is intended to encompass, for example, $C_1$, $C_2$, $C_3$, $C_4$, etc., as well as $C_{1-21}$, $C_{1-20}$, $C_{1-15}$, $C_{1-10}$, $C_{2-20}$, $C_{2-15}$, $C_{2-10}$, $C_{3-15}$, $C_{3-10}$, etc. alkyl.

As used herein, "alkyl" refers to a radical of a straight-chain or branched saturated hydrocarbon group having from, in some embodiments, 1 to 4 carbon atoms ("$C_{1-4}$ alkyl"), and in other embodiments 1 to 22 carbon atoms ("$C_{1-22}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 4 carbon atom ("$C_{2-4}$ alkyl"). In yet other embodiments, an alkyl group has 1 to 21 carbon atoms ("$C_{1-21}$ alkyl"), 1 to 20 carbon atoms ("$C_{1-20}$ alkyl"), 1 to 15 carbon atoms ("$C_{1-15}$ alkyl"), 1 to 10 carbon atoms ("$C_{1-10}$ alkyl"), etc. Examples of such alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), pentyl ($C_5$), and the like.

As used herein, "alkenyl" or "alkene" refers to a radical of a straight-chain or branched hydrocarbon group having from, in some embodiments, 2 to 4 carbon atoms ("$C_{2-4}$ alkenyl"), and in other embodiments 2 to 22 carbon atoms ("$C_{2-22}$ alkenyl"), and one or more carbon-carbon double bonds. In some embodiments, an alkenyl group has 2 to 3 carbon atoms ("$C_{2-3}$ alkenyl"). In some embodiments, an alkenyl group has 2 carbon atoms ("$C_2$ alkenyl"). In yet other embodiments, an alkenyl group has 2 to 21 carbon atoms ("$C_{2-21}$ alkenyl"), 2 to 20 carbon atoms ("$C_{2-20}$ alkenyl"), 2 to 15 carbon atoms ("$C_{2-15}$ alkenyl"), 2 to 10 carbon atoms ("$C_{2-10}$ alkyl"), etc. The one or more carbon-carbon double bonds can be internal (such as in 2-butenyl) or terminal (such as in 1-butenyl). Examples of such alkenyl groups include ethenyl ($C_2$), 1-propenyl ($C_3$), 2-propenyl ($C_3$), 1-butenyl ($C_4$), 2-butenyl ($C_4$), butadienyl ($C_4$), 1-pentenyl ($C_5$), 2-pentenyl ($C_5$), and the like.

As used herein, "alkynyl" or "alkyne" refers to a radical of a straight-chain or branched hydrocarbon group having from 2 to 4 carbon atoms and one or more carbon-carbon triple bonds ("$C_{2-10}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

Examples

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Example.

Compound Chemistry

In accordance with the following methods and Examples, the following compounds were prepared:

Scheme 1

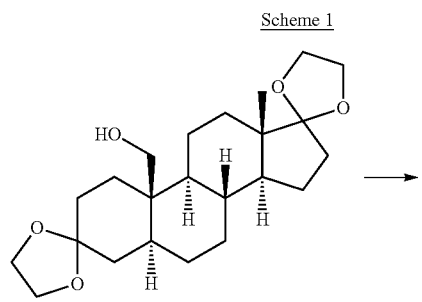

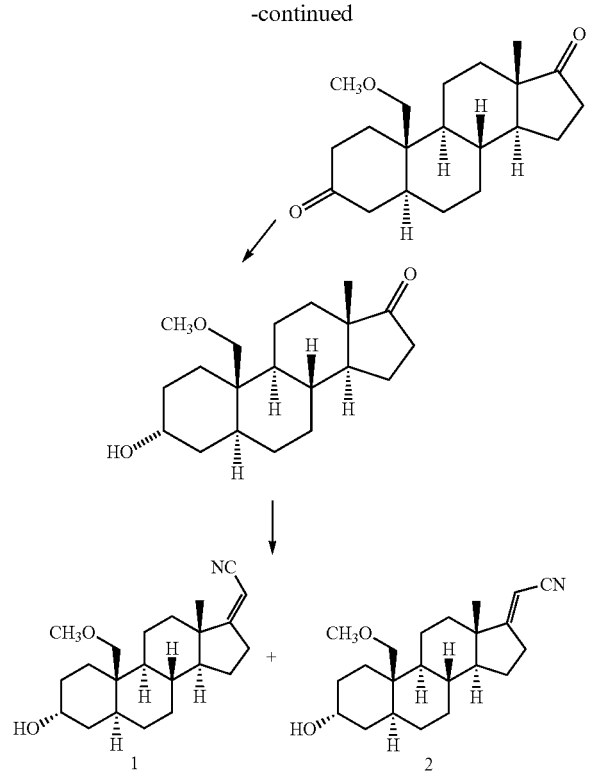

Compounds 1-2 were prepared using methods known in the art (see Hauser, et al., "Steroids. CCV. Fragmentations and intramolecular abstractions of tertiary hydrogen atoms by primary oxy radicals with fixed reaction centers," *Helv. Chim. Acta*, Vol. 47, pages 1961-1979 (1964)), and as further detailed herein below.

(5α)-19-Methoxyandrostane-3,17-dione, cyclic bis(1,2-ethanediyl acetal)

A mixture of the known 19-hydroxyandrostane-3,17-dione, cyclic bis(1,2-ethanediyl) acetal (430 mg, 1.1 mmol), NaH (200 mg, 5 mmol) and THF (10 mL) was heated at reflux for 2 h under $N_2$. The reaction mixture was cooled to room temperature, and methyl iodide (2 mL, 32 mmol) was added and the mixture was stirred at room temperature for 13 h. The reaction mixture was cooled to 0° C. and excess NaH was carefully quenched by adding MeOH (2 mL). Water (100 mL) was added and the product was extracted into EtOAc (80 mL×3). The combined organic extracts were washed with brine, dried and concentrated to give a colorless liquid. The crude product was purified by flash column chromatography (silica gel eluted with 15-20% EtOAc in hexanes) to give the product as a colorless liquid (440 mg, 99%): IR $\lambda_{max}$ 2923, 1457, 1378, 1306, 1210 cm$^{-1}$; $^1$H NMR δ 3.89 (s, 4H), 3.87-3.82 (m, 4H), 3.47 (d, J=10.0 Hz), 3.39 (d, J=9.9 Hz), 3.25 (s, 3H), 0.82 (s, 3H); $^{13}$C NMR δ 119.3, 109.2, 71.0, 65.0, 64.5, 64.0, 59.0, 54.0, 50.4, 46.0, 43.8, 38.9, 38.4, 36.2, 34.1, 31.5, 31.1, 31.0 (2×C), 29.6, 28.1, 22.6, 21.7, 14.4. Anal. Calcd for: $C_{24}H_{38}O_5$: C, 70.90%; H, 9.42%. Found: C, 71.17%; H, 9.53%.

(5α)-19-Methoxyandrostane-3,17-dione

A mixture of the 19-methoxy bisketal (400 mg, 0.98 mmol), PTSA (100 mg), acetone (8 mL) and water (0.5 mL)

was stirred at room temperature for 14 h. The reaction was neutralized with aqueous NaHCO$_3$ and the acetone was removed under reduced pressure. Water (80 mL) was added and the product was extracted into EtOAc (60 mL×3). The combined EtOAc extracts were dried and concentrated to give a white solid which was purified by flash column chromatography (silica gel eluted with 20-30% EtOAc in hexanes) to yield the 19-methoxy diketone product (230 mg, 73%): mp 94-96° C.; IR λmax 2918, 1738, 1712, 1452, 1407, 1373, 1270, 1248, 1220, 1202 cm$^{-1}$; $^1$H NMR δ 3.60 (d, 1H, J=11.0 Hz), 3.57 (d, 1H, J=11.0 Hz), 3.26 (s, 3H), 0.82 (s, 3H); $^{13}$C NMR δ 220.5, 211.7, 71.7, 59.0, 53.9, 51.3, 47.6, 46.1, 44.7, 38.9, 38.5, 35.6, 35.3, 34.2, 31.5, 30.3, 28.1, 21.5, 21.3, 13.7. HRMS Calcd for C$_{20}$H$_{30}$O$_3$: 318.2195. Found: 318.2180.

(3α,5α)-3-Hydroxy-19-methoxyandrostan-17-one

A 1 M K-Selectride® solution in THF (2 mL, 2 mmol, 3 eq) was added to a cold solution (-78° C.) of the 19-methoxy diketone (210 mg, 0.66 mmol) in THF (5 mL) and the reaction was stirred at -78° C. for 1.5 h. The reaction was quenched by adding a few drops of acetone and then allowed to warm to room temperature. 3 N aqueous NaOH (10 mL) followed by 30% aqueous H$_2$O$_2$ (10 mL) was added and the reaction was stirred at room temperature for 1.5 h. The product was extracted into EtOAc (3×60 mL) and the combined EtOAc extracts were washed with brine, dried, and concentrated to give an off-white solid which was purified by flash column chromatography (silica gel eluted with 20-40% EtOAc in hexanes). The product (142 mg, 67%) had: mp 172-174° C.; IR λmax 3436, 2921, 1738, 1453, 1406, 1372, 1248, 1203 cm$^{-1}$; $^1$H NMR δ 4.05 (b s, 1H), 3.48 (d, 1H, J=9.9 Hz), 3.38 (d, J=10.2 Hz), 3.25 (s, 3H), 2.39 (1H, dd, J=19.3, 8.8 Hz), 0.84 (s, 3H) $^{13}$C NMR δ 221.5, 71.1, 66.1, 59.0, 54.6, 51.7, 47.8, 39.6, 39.2, 36.0, 35.7, 35.5, 31.8, 30.7, 29.2, 27.9, 27.1, 21.6, 21.1, 13.8. Anal. Calcd for C$_{20}$H$_{32}$O$_3$: C, 74.96%; H, 10.06%. Found: C, 74.91%; H, 9.86%.

[3α,5α,17(20)Z]-19-methoxypregn-17(20)-ene-21-nitrile (Compound 1) and [3α,5α,17(20)E]-19-methoxypregn-17(20)-ene-21-nitrile (Compound 2)

Diethyl(cyanomethyl)phosphonate (0.83 mL, 5.13 mmol) was added dropwise to a suspension of NaH (60% dispersion in oil, 200 mg, 5 mmol) in dry THF (5 mL) at 0° C. under N$_2$. After disappearance of the solid NaH, (3α,5α)-3-Hydroxy-19-methoxyandrostan-17-one (100 mg, 0.31 mmol) in dry THF (10 mL) was added. The reaction was allowed to warm to room temperature and stirred for another 15 h at room temperature. The reaction was quenched with aqueous NaHCO$_3$ and the product extracted into EtOAc. The combined EtOAc extracts were washed with brine and dried. After solvent evaporation, the residue was purified by column chromatography to give an inseparable mixture of the Compound 1 and Compound 2 stereoisomers (90 mg, 85%).

The unseparated Compound 1 and Compound 2 stereoisomers (60 mg, 0.17 mmol) were converted to their corresponding 3-acetate derivatives (66 mg, 100%) using standard acetylation conditions (AcOAc, Et$_3$N, 4-DMAP in CH$_2$Cl$_2$). The acetate derivatives were separated by preparative TLC (3 plates), eluting with CHCl$_3$. The separated stereoisomers were visualized using iodine vapors. Elution of the separated products from the TLC plate yielded pure 3-acetate derivative of Compound 1 (25 mg) and pure 3-acetate derivative of Compound 2 (20 mg) and some mixture of the unseparated 3-acetates (10 mg).

[3α,5α,17(20)Z]-19-methoxypregn-17(20)-ene-21-nitrile (Compound 1)

The 3-acetate derivative of the pure Compound 1 product (27 mg) was subjected to transesterification with MeOH using dry HCl/MeOH to obtain pure Compound 1 (22 mg, 92%): mp 166-168° C.; [α]$^{20}_D$ +36.7 (CHCl$_3$, c 0.08); IR λmax 3436, 2920, 2216, 1448, 1375, 1270 cm$^{-1}$; $^1$H NMR δ 5.09 (t, 1H, J=1.9 Hz), 4.10 (b s, 1H), 3.50 (d, 1H, J=10.2 Hz), 3.42 (d, 1H, J=10.2 Hz), 3.30 (s, 3H), 0.97 (s, 3H); $^{13}$C NMR δ 179.5, 116.7, 87.7, 71.2, 66.4, 59.1, 55.4, 54.3, 46.9, 39.6, 39.2, 36.1, 35.6, 35.1, 32.5, 31.7, 29.5, 28.1, 27.2, 23.7, 21.8, 17.0. Anal. Calcd for C$_{22}$H$_{33}$NO$_2$: C, 76.92%; H, 9.68%; N, 4.08%. Found: C, 76.78%; H, 9.47%; N, 4.06.

[3α,5α,17(20)E]-19-methoxypregn-17(20)-ene-21-nitrile (Compound 2)

The 3-acetate derivative of the pure Compound 2 (20 mg, top spot) was subjected to transesterification with MeOH using dry HCl/MeOH to obtain pure Compound 2 (17 mg, 96%): mp 185-188° C.; [α]$^{20}_D$ -16.4 (CHCl$_3$, c 0.15); IR λmax 3401, 2919, 2216, 1636, 1448, 1373 cm$^{-1}$; $^1$H NMR δ 4.99 (t, 1H, J=2.5 Hz), 4.10 (b s, 1H), 3.51 (d, 1H J=9.9 Hz), 3.42 (d, 1H, J=9.9 Hz), 3.30 (s, 3H), 2.80-2.50 (m, 2H), 0.85 (s, 3H); $^{13}$C NMR δ 181.2, 117.5, 71.1, 66.3, 59.1, 54.4, 54.2, 46.3, 39.7, 39.2, 36.1, 35.7, 35.01, 31.7, 30.2, 29.4, 28.0, 27.1, 23.7, 21.7, 18.1. Anal. Calcd for C$_{22}$H$_{33}$NO$_2$: C, 76.92%; H, 9.68%, N, 4.08%. Found: C, 76.74%; H, 9.73%; N, 3.96.

[$^{35}$S]-TBPS Displacement

The IC$_{50}$ values for the compounds of Scheme 1 (i.e., Compounds 1 and 2) as non-competitive displacers of [$^{35}$S]-TBPS from the picrotoxin binding site on GABA$_A$ receptors are reported in Table 1.

TABLE 1

Inhibition of [$^{35}$S]-TBPS Binding by Compounds 1 and 2

| Compound | IC$_{50}$ (nM) | n$_{Hill}$ |
|---|---|---|
| 1 | 42 ± 4 | 1.21 ± 0.11 |
| 2 | 657 ± 114 | 0.91 ± 0.11 |

The displacement of bound [$^{35}$S]-TBPS from GABA$_A$ receptors by Compound 1 are illustrated in FIG. 1, as well.

Results presented are from duplicate experiments performed in triplicate. Error limits are calculated as standard error of the mean. Methods used are known in the art (see, e.g., E. Stastna, et al., *Neurosteroid Analogues. 16. A New Explanation for the Lack of Anesthetic Effects in Δ$^{16}$-Alphaxalone and Identification of a Δ$^{17(20)}$ Analogue with Potent Anesthetic Activity*, J. Med. Chem., 54(11), pp. 3926-34 (2011)).

Electrophysiology Results

The compounds of the present disclosure were evaluated for the ability to potentiate chloride currents mediated by 2 μM GABA at rat α$_1$β$_2$γ$_{2L}$ type GABA$_A$ receptors expressed in *Xenopus laevis* oocytes and the results are shown in Table 2.

TABLE 2

Modulation of Rat $\alpha_1\beta_2\gamma_{2L}$
GABA$_A$ Receptor Function by Compounds 1 and 2

| Com-pound | oocyte electrophysiology[a] | | | (gating) |
|---|---|---|---|---|
| | 0.1 μM | 1 μM | 10 μM | 10 μM |
| 1 | 2.88 ± 0.90 | 15.27 ± 2.58 | 45.80 ± 15.79 | 0.19 ± 0.08 |
| 2 | 0.69 ± 0.11 | 1.26 ± 0.22 | 2.97 ± 0.33 | 0.31 ± 0.25 |

Figure 2:
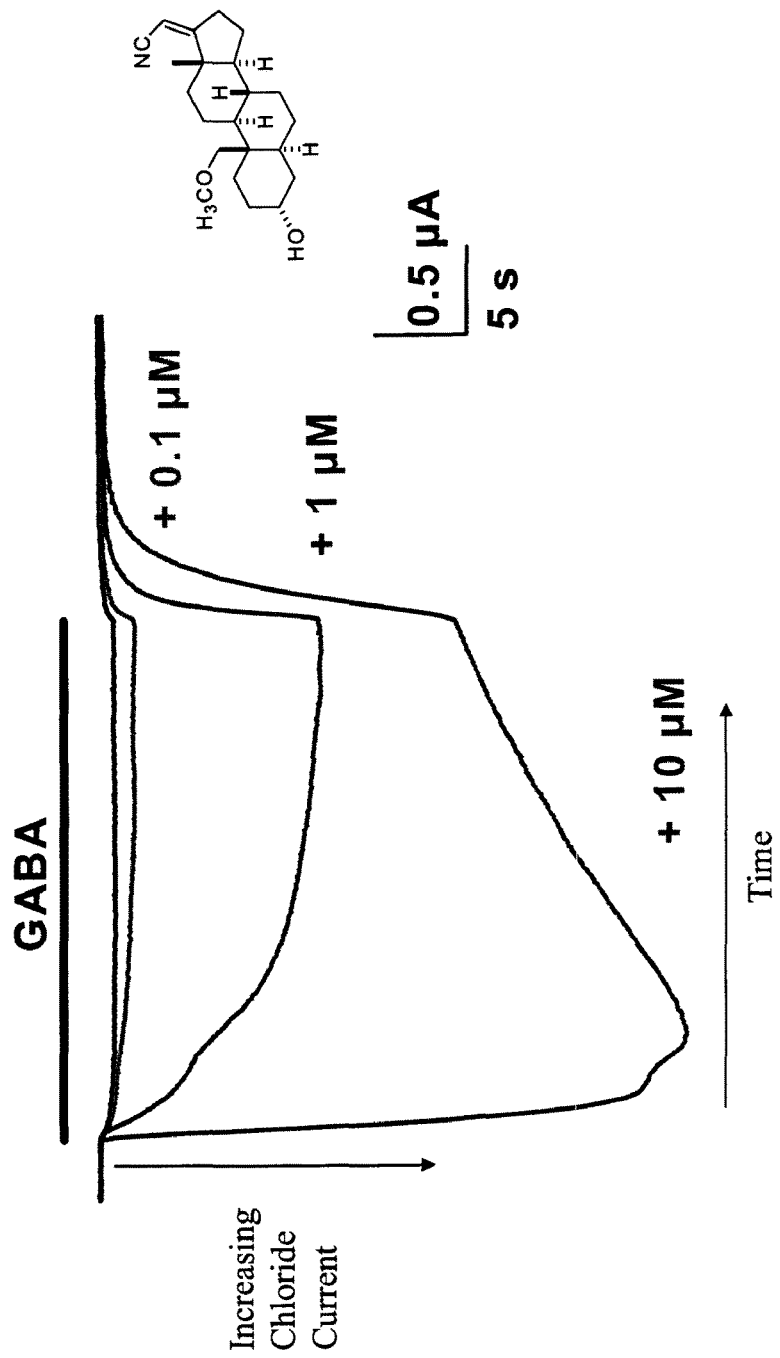
FIG. 2 is a graph illustrating the potentiation of 2 μM GABA-mediated chloride currents at rat α1β2γ2-type $GABA_A$ receptors expressed in frog oocytes by different concentrations of Compound 1.

The potentiation of 2 μM GABA-mediated chloride currents at rat $\alpha1\beta2\gamma2$-type GABA$_A$ receptors expressed in frog oocytes by different concentrations of Compound 1, is illustrated by the curves in FIG. 2, as well.

[a]The GABA concentration used for the control response was 2 μM. Each compound was evaluated on at least four different oocytes at the concentrations indicated, and the results reported are the ratio of currents measured in the presence/absence of added compound. Gating represents direct current gated by 10 μM compound in the absence of GABA, and this current is reported as the ratio of compound only current/2 μM GABA current. Error limits are calculated as standard error of the mean (N≥4). Methods used are known in the art (see, e.g., E. Stastna, et al., *Neurosteroid Analogues. 16. A New Explanation for the Lack of Anesthetic Effects in $\Delta^{16}$-Alphaxalone and Identification of a $\Delta^{17(20)}$ Analogue with Potent Anesthetic Activity*, J. Med. Chem., 54(11), pp. 3926-34 (2011)).

Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Effects of Compounds 1 and 2[a]

| Com-pound[a] | Tadpole LRR EC$_{50}$ (μM) | Tadpole LRR n$_{Hill}$ | Tadpole LSR EC$_{50}$ (μM) | Tadpole LSR n$_{Hill}$ |
|---|---|---|---|---|
| 1 | 0.159 ± 0.025 | −1.32 ± 0.23 | 0.970 ± 0.065 | −20.0 ± 0.43 |
| 2 | 2.78 ± 0.56 | −1.97 ± 0.65 | ~10 μM | — |

Figure 3:
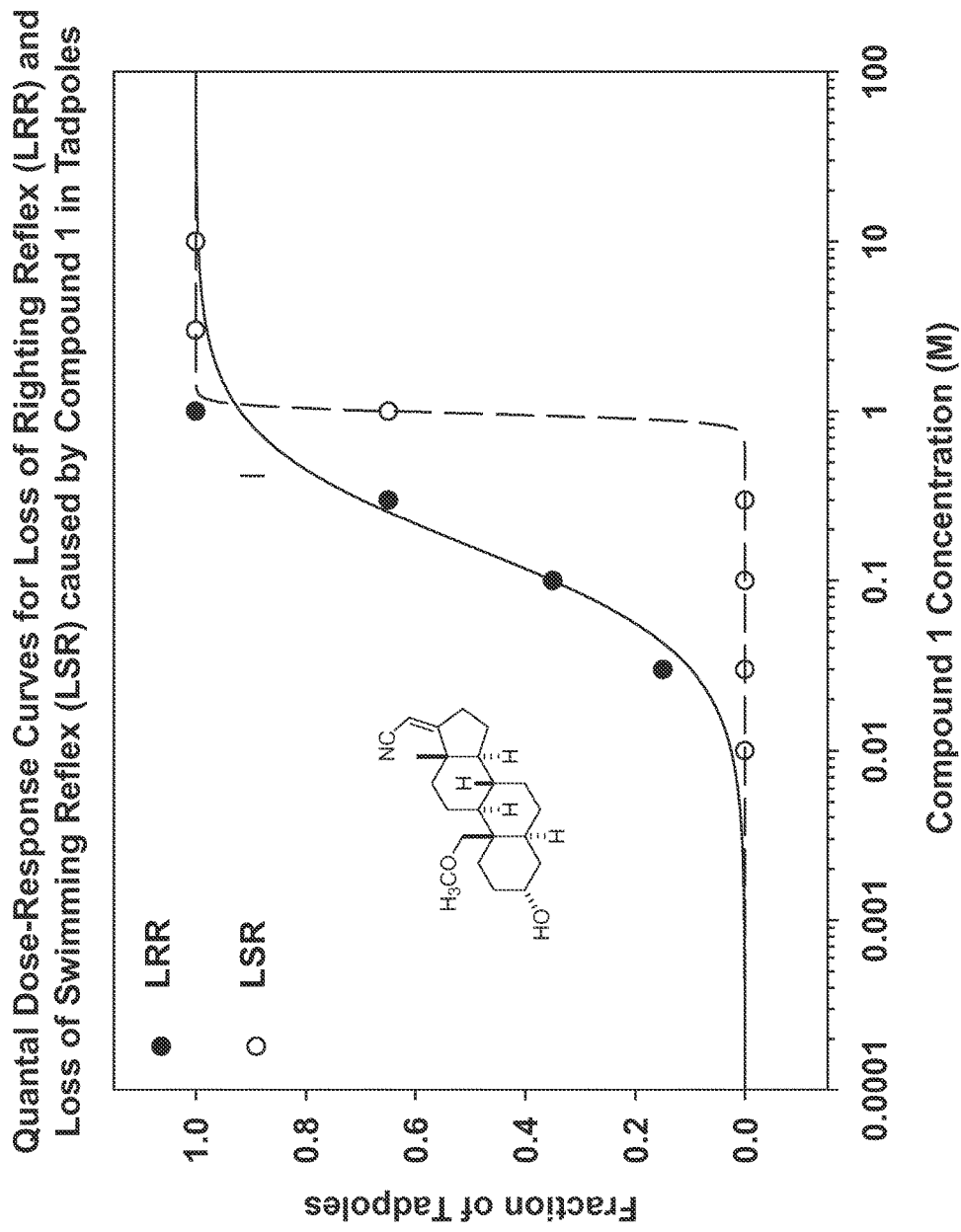
FIG. 3 is a graph containing a quantal dose-response curve for Loss of Righting Reflex (LRR) and Loss of Swimming Reflex (LSR) caused by Compound 1 in tadpoles.

A quantal dose-response curve for loss of righting reflect (LRR) and loss of swimming reflex (LSR) caused by Compound 1 in tadpoles, is illustrated in FIG. 3, as well.

[a]Methods used are known in the art (see, e.g., E. Stastna, et al., *Neurosteroid Analogues. 16. A New Explanation for the Lack of Anesthetic Effects in $\Delta^{16}$-Alphaxalone and Identification of a $\Delta^{17(20)}$ Analogue with Potent Anesthetic Activity*, J. Med. Chem., 54(11), pp. 3926-34 (2011)). Error limits are calculated as standard error of the mean (N=10 or more animals at each of five or more different concentrations).

General Methods

The compounds discussed in the present disclosure were produced as discussed elsewhere throughout this disclosure and by the following methods.

Solvents were either used as purchased or dried and purified by standard methodology. Extraction solvents were dried with anhydrous Na$_2$SO$_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in CDCl$_3$ at ambient temperature at 300 MHz ($^1$H) or 74 MHz ($^{13}$C). Purity was determined by TLC on 250 μm thick Uniplates™ from Analtech (Newark, Del.). All pure compounds (purity>95%) gave a single spot on TLC. Elemental analyses were performed by M-H-W Laboratories (Phoenix, Ariz.).

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A method of inducing anesthesia in a subject in need thereof, the method comprising administering to the subject a therapeutically effective amount of a compound of Formula (I), wherein Formula (I) is:

(I)

or a pharmaceutically acceptable salt thereof;
wherein:
R$_1$ is H;
R$_2$ is =O, H, or OR$_a$, where R$_a$ is selected from H, optionally substituted C$_1$-C$_4$ alkyl, or optionally substituted aryl, with the proviso that when R$_2$ is =O, R$_8$ is not present;
R$_3$ is H, optionally substituted C$_1$-C$_4$ alkyl, optionally substituted C$_2$-C$_4$ alkenyl, optionally substituted C$_2$-C$_4$ alkynyl, or optionally substituted aryl;
R$_4$ is independently selected from H and unsubstituted C$_1$-C$_4$ alkyl;
R$_5$ is substituted C$_1$-C$_4$ alkyl, optionally substituted C$_2$-C$_4$ alkenyl, or optionally substituted C$_2$-C$_4$ alkynyl;
R$_6$ is H, optionally substituted C$_1$-C$_4$ alkyl, optionally substituted C$_1$-C$_4$ alkoxy;
R$_7$ is H, optionally substituted C$_1$-C$_4$ alkoxy, or an optionally substituted morpholinyl ring;
R$_8$, when present, is H or optionally substituted C$_1$-C$_4$ alkyl; and,
- - - denotes an optional, additional C—C bond, resulting in either a C=C bond between C$_4$-C$_5$ or C$_5$-C$_6$, with the proviso that when present, the C$_5$—H substituent is not present.

2. The method according to claim 1, wherein one or both of R$_6$ or R$_7$, when present and other than H, are in the beta configuration.

3. The method according to claim 1, wherein the R$_3$ group is selected from the group consisting of H, methyl, and trifluoromethyl.

4. The method according to claim 1, wherein R$_7$ is selected from the group consisting of H, methoxy, ethoxy, and an optionally substituted morpholinyl ring.

5. The method according to claim 1, wherein $R_5$ is substituted methyl.

6. The method according to claim 1, wherein $R_6$ is H.

7. The method according to claim 1, wherein $R_2$ is =O, methoxy or H.

8. The method according to claim 1, wherein $R_4$ is methyl.

9. The method according to claim 1, having Formula (I-a):

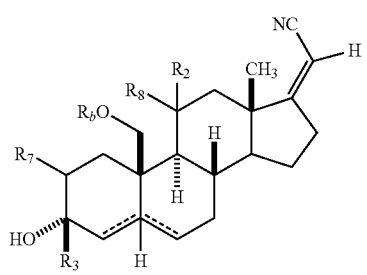

(I-a)

or a pharmaceutically acceptable salt thereof, wherein $R_b$ is optionally substituted $C_1$-$C_4$ alkyl.

10. The method according to claim 1, having Formula (I-j):

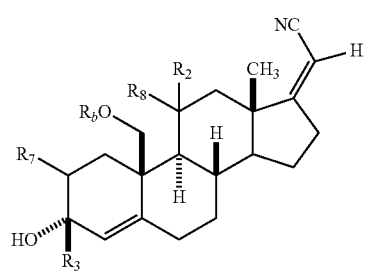

(I-j)

or a pharmaceutically acceptable salt thereof, wherein $R_b$ is optionally substituted $C_1$-$C_4$ alkyl.

11. The method according to claim 1, having Formula (I-k):

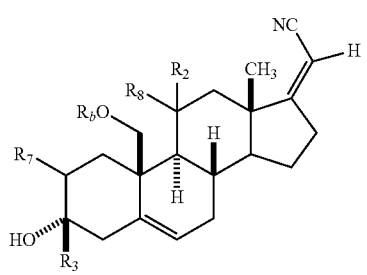

(I-k)

or a pharmaceutically acceptable salt thereof, wherein $R_b$ is optionally substituted $C_1$-$C_4$ alkyl.

12. The method according to claim 1, having a formula selected from the group consisting: of:

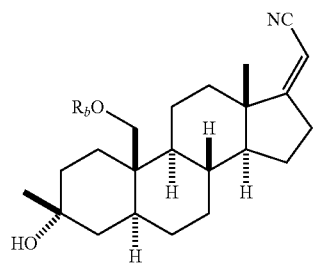

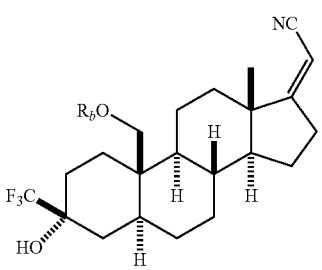

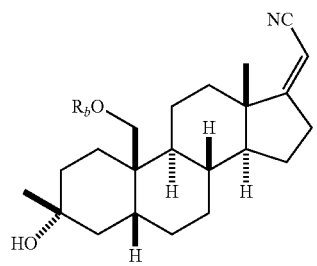

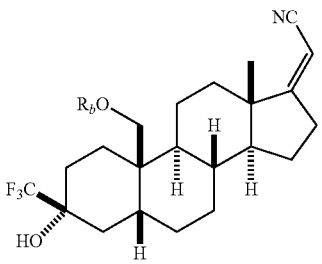

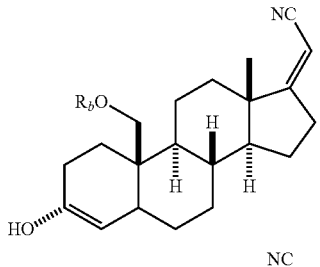

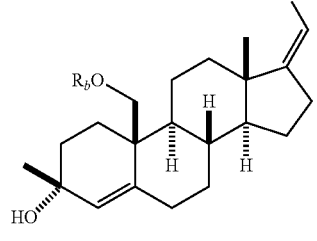

-continued

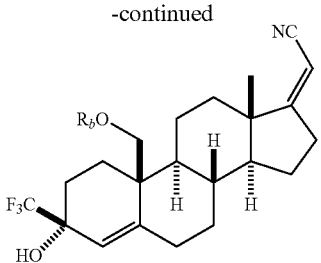

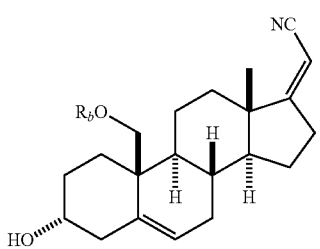

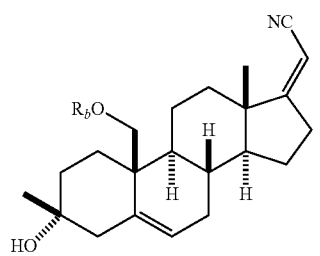

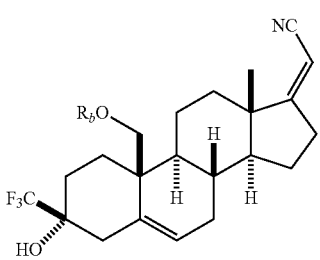

and pharmaceutically acceptable salts thereof, wherein $R_b$ is optionally substituted $C_1$-$C_4$ alkyl.

13. The method according to claim 1, having the structure:

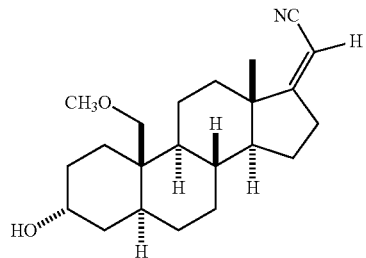

or a pharmaceutically acceptable salt thereof.

14. A method of inducing anesthesia in a subject in need thereof, the method comprising administering to the subject a therapeutically effective amount of a compound of Formula (II), wherein Formula (II) is

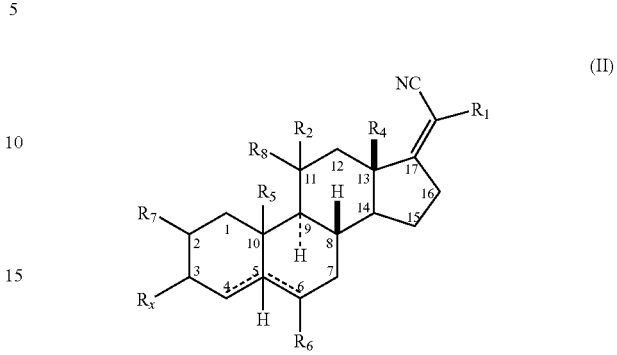

or a pharmaceutically acceptable salt thereof;

wherein:

$R_1$ is H;

$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;

$R_x$ is =O or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration (and when $R_x$ is $R_d$, with $R_d$ being $C(O)R_e$, then it is preferably in the beta configuration);

$R_4$ is independently selected from H and unsubstituted $C_1$-$C_4$ alkyl;

$R_5$ is substituted $C_1$-$C_4$ alkyl, optionally substituted $C_2$-$C_4$ alkenyl, or optionally substituted $C_2$-$C_4$ alkynyl;

$R_6$ is H, optionally substituted $C_1$-$C_4$ alkyl, or optionally substituted $C_1$-$C_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl; and,

- - - denotes an optional, additional C—C bond, resulting in either a C=C bond between $C_4$-$C_5$ or $C_5$-$C_6$, with the proviso that when present, the $C_5$—H substituent is not present.

15. The method according to claim 14, wherein $R_x$ is OH in the beta configuration.

16. The method according to claim 14, wherein $R_x$ is =O.

17. The method according to claim 14, wherein $R_7$ is selected from the group consisting of H, methoxy, ethoxy, and an optionally substituted morpholinyl ring.

18. The method according to claim 14, wherein $R_5$ is substituted methyl.

19. The method according to claim 14, wherein $R_6$ is H.

20. The method according to claim 14, wherein $R_2$ is =O, methoxy or H.

21. The method according to claim 14, wherein $R_4$ is methyl.

22. The method according to claim 14, having Formula (II-a):

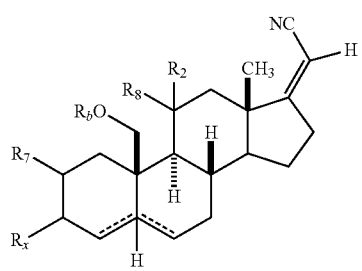
(II-a)

or a pharmaceutically acceptable salt thereof, wherein $R_b$ is optionally substituted $C_1$-$C_4$ alkyl.

23. The method according to claim 14, having Formula (II-j):

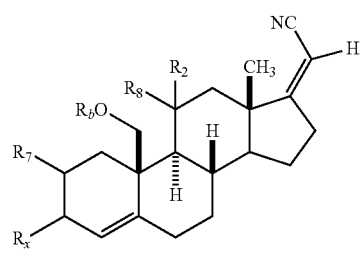
(II-j)

or a pharmaceutically acceptable salt thereof, wherein $R_b$ is optionally substituted $C_1$-$C_4$ alkyl.

24. The method according to claim 14, having Formula (II-k):

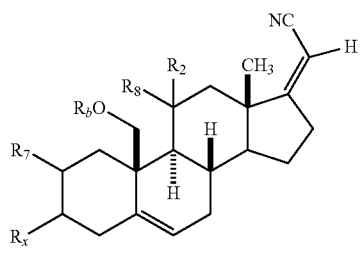
(II-k)

or a pharmaceutically acceptable salt thereof, wherein $R_b$ is optionally substituted $C_1$-$C_4$ alkyl.

25. The method according to claim 14, having a formula selected from the group consisting of:

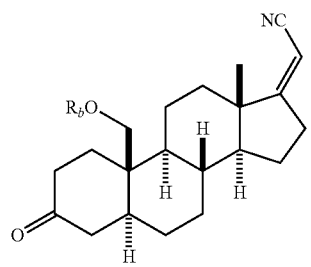

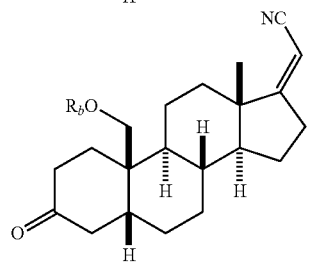

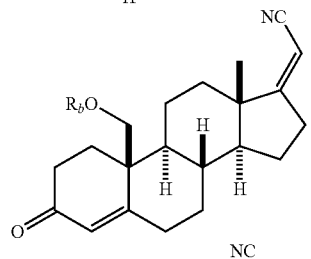

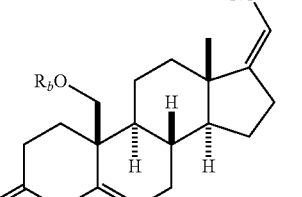
and

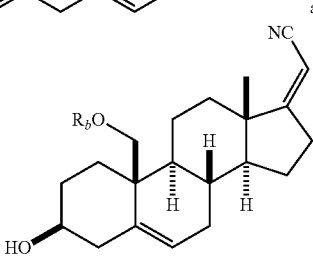

and pharmaceutically acceptable salts thereof, wherein $R_b$ is optionally substituted $C_1$-$C_4$ alkyl.

* * * * *